(12) United States Patent
Broderick et al.

(10) Patent No.: US 10,889,534 B2
(45) Date of Patent: Jan. 12, 2021

(54) ALKYLATION PROCESSES USING LIQUID LEWIS ACID CATALYSTS

(71) Applicant: UOP LLC, Des Plaines, IL (US)

(72) Inventors: Erin M. Broderick, Arlington Heights, IL (US); Alakananda Bhattacharyya, Glen Ellyn, IL (US); Peter K. Coughlin, Mundelein, IL (US)

(73) Assignee: UOP LLC, Des Plains (IL)

( * ) Notice: Subject to any disclaimer, the term of this patent is extended or adjusted under 35 U.S.C. 154(b) by 0 days.

(21) Appl. No.: 15/867,445

(22) Filed: Jan. 10, 2018

(65) Prior Publication Data

US 2018/0127335 A1    May 10, 2018

Related U.S. Application Data

(63) Continuation of application No. PCT/US2016/040974, filed on Jul. 5, 2016.
(Continued)

(51) Int. Cl.
*C07C 2/62* (2006.01)
*C07C 2/70* (2006.01)
(Continued)

(52) U.S. Cl.
CPC .............. *C07C 2/62* (2013.01); *B01J 27/125* (2013.01); *B01J 31/0231* (2013.01); *B01J 31/0235* (2013.01); *B01J 31/2208* (2013.01); *B01J 31/4015* (2013.01); *C07C 2/60* (2013.01); *C07C 2/68* (2013.01); *C07C 2/70* (2013.01); *B01J 27/128* (2013.01); *B01J 31/0204* (2013.01); *B01J 31/0209* (2013.01);
(Continued)

(58) Field of Classification Search
CPC .................................................. B01J 31/0231
See application file for complete search history.

(56) References Cited

U.S. PATENT DOCUMENTS

| 3,697,617 A | 10/1972 | Yoo et al. |
| 4,764,440 A | 8/1988 | Jones et al. |

(Continued)

FOREIGN PATENT DOCUMENTS

| CA | 2863836 | 8/2013 |
| EP | 0819667 A2 | 1/1998 |

(Continued)

OTHER PUBLICATIONS

Pang et al. "Mixed Chlorometallate Ionic Liquids as C4 alkylation catalysts: A Quantitative Study of Acceptor Properties" Catalysts 2018, 8, 498. (Year: 2018).*

(Continued)

*Primary Examiner* — Philip Y Louie
*Assistant Examiner* — Alyssa L Cepluch

(57) ABSTRACT

An alkylation process is described. The alkylation process includes contacting a feed comprising a paraffin or an aromatic with an olefin feed in the presence of a liquid Lewis acid catalyst in an alkylation reaction zone under alkylation conditions to form a reaction mixture comprising alkylation products and the liquid Lewis acid catalyst. The liquid Lewis acid catalyst is the liquid reaction product of a donor molecule and a metal halide. The alkylation products are separated from the liquid Lewis acid catalyst and recovered.

19 Claims, 1 Drawing Sheet

Related U.S. Application Data

(60) Provisional application No. 62/190,960, filed on Jul. 10, 2015.

(51) Int. Cl.

| | | |
|---|---|---|
| *B01J 27/125* | (2006.01) | |
| *B01J 31/02* | (2006.01) | |
| *B01J 31/40* | (2006.01) | |
| *C07C 2/60* | (2006.01) | |
| *B01J 31/22* | (2006.01) | |
| *C07C 2/68* | (2006.01) | |
| *B01J 27/128* | (2006.01) | |

(52) U.S. Cl.
CPC ........ *B01J 31/0222* (2013.01); *B01J 31/0247* (2013.01); *C07C 2527/125* (2013.01); *C07C 2531/02* (2013.01); *Y02P 20/584* (2015.11)

(56) References Cited

U.S. PATENT DOCUMENTS

| | | | |
|---|---|---|---|
| 5,104,840 A | 4/1992 | Chauvin et al. | |
| 5,292,982 A * | 3/1994 | Del Rossi | B01J 27/06 |
| | | | 502/150 |
| 5,406,018 A | 4/1995 | Sherman | |
| 5,510,561 A | 4/1996 | Sherman et al. | |
| 5,824,832 A | 10/1998 | Sherif et al. | |
| 6,106,789 A * | 8/2000 | Thompson | B01J 19/24 |
| | | | 165/145 |
| 7,651,970 B2 | 1/2010 | Elomari et al. | |
| 7,674,739 B2 | 3/2010 | Elomari et al. | |
| 7,674,740 B2 | 3/2010 | Harris et al. | |
| 7,678,727 B2 | 3/2010 | Harris et al. | |
| 7,691,771 B2 | 4/2010 | Harris et al. | |
| 7,727,925 B2 | 6/2010 | Elomari et al. | |
| 7,732,363 B2 | 6/2010 | Elomari et al. | |
| 7,737,067 B2 | 6/2010 | Elomari et al. | |
| 7,825,055 B2 | 11/2010 | Elomari et al. | |
| 7,956,002 B2 | 6/2011 | Elomari et al. | |
| 8,518,298 B2 * | 8/2013 | Abbott | C25C 3/00 |
| | | | 252/183.13 |
| 8,524,623 B2 | 9/2013 | Timken et al. | |
| 9,079,175 B1 | 7/2015 | Smith et al. | |
| 9,079,176 B1 | 7/2015 | Smith et al. | |
| 9,120,092 B1 | 9/2015 | Broderick et al. | |
| 9,221,043 B2 | 12/2015 | Broderick et al. | |
| 2007/0225538 A1 * | 9/2007 | Elomari | C07C 2/60 |
| | | | 585/727 |
| 2013/0001092 A1 * | 1/2013 | Abbott | C07C 233/05 |
| | | | 205/238 |
| 2013/0217847 A1 | 8/2013 | Wettling et al. | |
| 2016/0052838 A1 * | 2/2016 | Atkins | C10M 105/04 |
| | | | 585/511 |
| 2017/0203286 A1 * | 7/2017 | Uppara | C07C 67/293 |

FOREIGN PATENT DOCUMENTS

| | | | |
|---|---|---|---|
| EP | 0631567 B1 | 3/2000 | |
| EP | 2646478 | 10/2013 | |
| WO | 1994014734 A1 | 7/1994 | |
| WO | WO-9414734 A1 * | 7/1994 | ............. C07C 2/62 |
| WO | 2009002967 A2 | 12/2008 | |
| WO | 2014167331 | 10/2014 | |
| WO | 2014167332 | 10/2014 | |

OTHER PUBLICATIONS

Matuszek et al. "Friedel-Crafts alkylation catalysed by GaCl3-based liquid coordination complexes" Green Chemistry 2015, 17, 4255-4262. (Year: 2015).*
DeCastro et al. "Immobilised Ionic Liquids as Lewis Acid Catalysts for the Alkylation of Aromatic Compounds with Dodecene" Journal of Catalysis 196, 86-94 (2000). (Year: 2000).*
Hogg, "Liquid coordination complexes: a new class of Lewis acids as safer alternatives to BF3 in synthesis of polyalphaolefins," Green Chemistry (2015), 17(3), 1831-1841.
Search Report dated Nov. 17, 2016 for corresponding PCT Appl. No. PCT/US2016/040974.
International Preliminary Report on Patentability from corresponding PCT application No. PCT/US2016/040974, dated Jan. 16, 2018.
Written Opinion of the International Searching Authority from from corresponding PCT application No. PCT/040974, dated Nov. 17, 2016.
Coleman et al., "Liquid Coordination Complexes Formed by the Heterolytic Cleavage of Metal Halides", Chem. Int. Ed. (2013), v 52, p. 12582-12586.
Abood et al., "Do all ionic liquids need organic cations? Characterisation of [AlCl2nAmide]+AlCl4-and comparison with imidazolium based systems" Chem. Commun. (2011), v 47, p. 3523-3525.

* cited by examiner

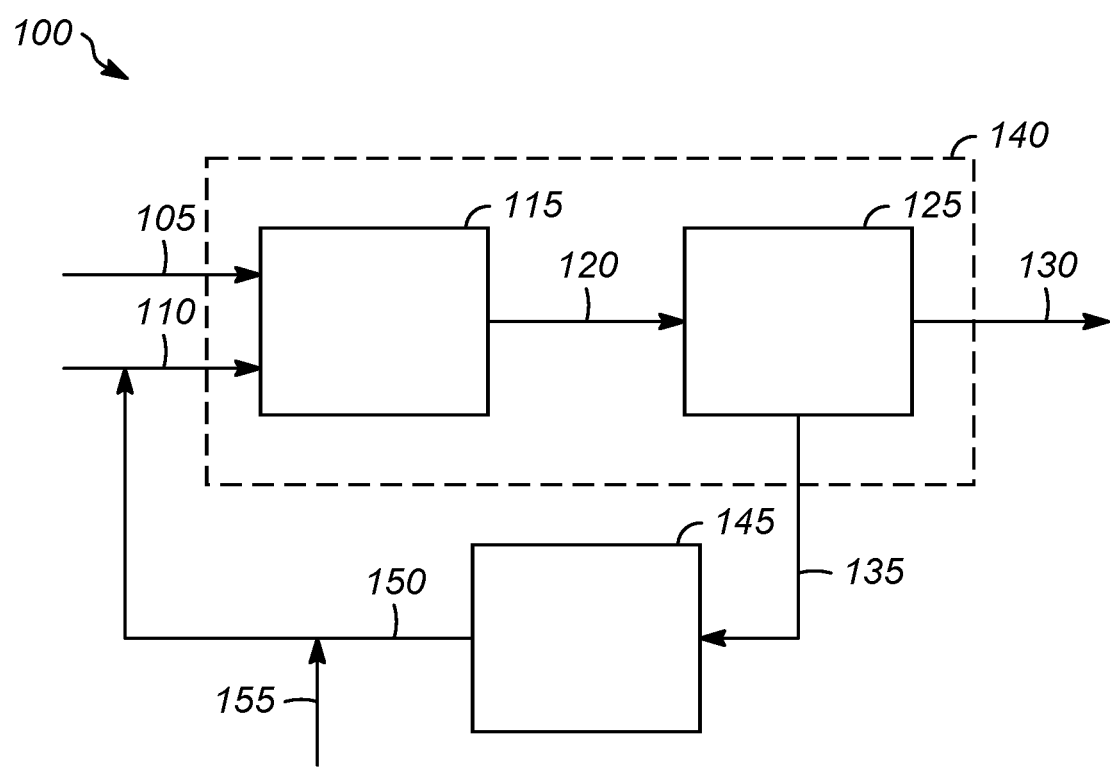

ALKYLATION PROCESSES USING LIQUID LEWIS ACID CATALYSTS

CROSS-REFERENCE TO RELATED APPLICATIONS

This application is a Continuation of International Application No. PCT/US2016/040974 filed Jul. 5, 2016 which application claims benefit of U.S. Provisional Application No. 62/190,960 filed Jul. 10, 2015, the contents of which cited applications are hereby incorporated by reference in their entirety.

BACKGROUND OF THE INVENTION

One example of a hydrocarbon conversion process is alkylation. Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. toluene, xylenes, ethylbenzene, etc.).

The alkylation of paraffins with olefins for the production of alkylate for gasoline can use a variety of catalysts. The choice of catalyst depends on the end product a producer desires. Typical alkylation catalysts include concentrated sulfuric acid or hydrofluoric acid. However, sulfuric acid and hydrofluoric acid are hazardous and corrosive, and their use in industrial processes requires a variety of environmental controls.

Solid catalysts are also used for alkylation. However, solid catalysts are generally rapidly deactivated by the presence of water, which may be present in the feed.

Acidic ionic liquids can be used as an alternative to the commonly used strong acid catalysts in hydrocarbon conversion processes such as alkylation. Ionic liquids are salts comprised of cations and anions which typically melt below about 100° C. Ionic liquids are essentially salts in a liquid state, and are described in U.S. Pat. Nos. 4,764,440, 5,104,840, and 5,824,832. The properties vary extensively for different ionic liquids, and the use of ionic liquids depends on the properties of a given ionic liquid. Depending on the organic cation of the ionic liquid and the anion, the ionic liquid can have very different properties.

Ionic liquid catalysts have been shown to be active, alkylation catalysts, even at temperatures below 25° C. This requires cooling the reactor and reactor feeds, which adds substantial cost to an alkylation process utilizing ionic liquids in the form of additional equipment and energy. The most common ionic liquid catalyst precursors for alkylation include imidazolium, or pyridinium-based cations coupled with the chloroaluminate anion ($Al_2Cl_7-$). In addition, ionic liquids are expensive materials that can be viscous, which has limited their use in alkylation processes.

There is a need for catalysts that cost less than ionic liquids and have a lower viscosity.

SUMMARY OF THE INVENTION

One aspect of the present invention is an alkylation process. In one embodiment, the alkylation process includes contacting a feed comprising a paraffin or an aromatic with an olefin feed in the presence of a liquid Lewis acid catalyst in an alkylation reaction zone under alkylation conditions to form a reaction mixture comprising alkylation products and the liquid Lewis acid catalyst. The liquid Lewis acid catalyst is the liquid reaction product of a donor molecule and a metal halide. The alkylation products are separated from the liquid Lewis acid catalyst and recovered.

BRIEF DESCRIPTION OF THE DRAWING

The FIGURE illustrates one embodiment of an alkylation process.

DETAILED DESCRIPTION OF THE INVENTION

The present invention involves the use of liquid Lewis acids as catalysts for alkylation processes. Liquid Lewis acid catalysts can be used as low cost alternatives to ionic liquid catalysts. A liquid Lewis acid is the liquid reaction product of a donor molecule and a metal halide. A donor molecule is a Lewis base that is able to donate electrons to the metal.

Examples of donor molecules are molecules having oxygen, sulfur, nitrogen, or phosphorus atoms. Suitable donor molecules include, but are not limited to, N,N-dimethylacetamide, N,N-dimethylformamide, N,N-dimethysulfoxide, caprolactam, N-methylcaprolactam, N-methylpyrrolidone, delta-valerolactone, tetrahydrofuran, diethyl ether, acetamide, caprolactone, delta-valerolactam, alpha-acetolactone, beta-propiolactone, gamma-butyrolactone, morpholine, beta-propiolactam, gamma-butyrolactam, delta-valerolactam, urea, trioctylphosphine oxide, thiourea, trioctylphosphine, thioacetamide, N-methylthioacetamide, N,N-dimethylthioacetamide or combinations thereof.

The metal halide comprises a metal and a halide. Suitable metals include, but are not limited to, Sn, Al, Zn, Mn, Fe, Ga, Cu, Ni, Co, In, or combinations thereof. The halide can include Br, Cl, I, F, or combinations thereof. Suitable metal halides include, but are not limited to, $AlCl_3$, $AlCl_2Br$, $AlBr_3$, $GaCl_3$, $GaCl_2Br$, $FeCl_3$, $GaBr_3$, $InCl_3$, $InBr_3$, $InCl_2Br$, or combinations thereof.

In some embodiments, the mole fraction of metal halide in the liquid Lewis acid is greater than about 0.5 to less than about 1, or about 0.6 to about 0.75.

The hydrocarbon feed and olefin feed are contacted with the liquid Lewis acid in the alkylation reaction zone. The hydrocarbon feed and the olefin feed can be mixed in the alkylation reaction zone or prior to entering the alkylation reaction zone. The alkylation reaction zone is under the appropriate conditions for alkylation. A reaction mixture is formed including the alkylation products, the liquid Lewis acid, and any unreacted hydrocarbon feed.

In some embodiments, a metal, an acid, or an acid precursor can be added to the alkylation reaction zone.

The alkylation products (and any unreacted hydrocarbon feed) can be separated from the liquid Lewis acid catalyst, which can then be regenerated using a suitable regeneration process. Suitable separation processes include, but are not limited to, gravity settling and fractionation due to density differences between the alkylation products and the liquid Lewis acid catalyst. Suitable regeneration processes include those used for regenerating ionic liquids. The regenerated liquid Lewis acid catalyst can be recycled to the reaction zone.

The alkylation products can also be separated from the unreacted hydrocarbon feed, such as the paraffin or aromatic. In some embodiments, this can be done after separating the alkylation products from the liquid Lewis acid.

Suitable separation processes include, but are not limited to, fractionation, decantation, or combinations thereof.

The FIGURE illustrates one embodiment of an alkylation process 100 of the present invention. Hydrocarbon feed 105 and liquid Lewis acid 110 enter alkylation reaction zone 115. The liquid Lewis acid 110 catalyzes the alkylation reaction. The effluent 120 from the alkylation reaction zone 115 includes the alkylation reaction products, the liquid Lewis acid, and any unreacted hydrocarbon feed. The effluent 120 is sent to separation zone 125 where the reaction products 130 are separated from the liquid Lewis acid 135.

In some embodiments, the alkylation reaction zone 115 and the separation zone 125 are in separate vessels. In other embodiments, they are in the same vessel 140.

The liquid Lewis acid 135 can be recycled to the alkylation reaction zone 115. The liquid Lewis acid 135 can be sent to a regeneration zone 145 for regeneration if needed. The regenerated liquid Lewis acid 150 can be reactivated with an acid 155 if needed. The regenerated liquid Lewis acid 150 can be recycled to the alkylation reaction zone 115.

Alkylation reactions in liquid Lewis acid catalysts are biphasic and take place at the interface in the liquid state due to the low solubility of hydrocarbons in the liquid Lewis acid.

The reaction will proceed simply by contacting the hydrocarbon feed and the liquid Lewis acid catalyst. In some instances, the reaction rate may be too slow to be commercially viable. When mass transfer rate is controlling, the reaction rate can be substantially increased by increasing the mixing intensity of hydrocarbon feed and liquid catalyst. After a certain point, increasing the mixing intensity will not provide any additional benefit. Mixing intensity can be controlled using pumps, flow configurations, and baffles. Baffles help to prevent a vortex from forming in the reactor, which would reduce the amount of mixing.

The contacting step may be practiced in laboratory scale experiments through full scale commercial operations. The process may be operated in batch, continuous, or semi-continuous mode. The contacting step can take place in various ways, with both countercurrent and co-current flow processes being suitable.

The reaction time is a function of the degree of mixing, the reaction temperature, and the mass/volume ratio of liquid catalyst to hydrocarbon being reacted. Generally, increasing any of these conditions will increase the reaction rate.

The alkylation reaction using the liquid Lewis acid is carried out at mild temperatures, and is typically a two-phase reaction. In some embodiments, cooling may be needed. If cooling is needed, it can be provided using any known methods. The catalyst effects the alkylation of the hydrocarbon and the olefin.

Typical alkylation reaction conditions include a temperature in the range of about −20° C. to the decomposition temperature of the liquid Lewis acid, or about −20° C. to about 100° C., or about −20° C. to about 80° C., or about 0° C. to about 80° C., or about 20° C. to about 80° C. It is preferred to have liquid Lewis acid that maintains its liquid state through the operating temperature range.

The pressure is typically in the range of atmospheric (0.1 MPa(g)) to about 8.0 MPa(g), or about 0.3 MPa(g) to about 2.5 MPa(g). The pressure is preferably sufficient to keep the reactants in the liquid phase.

The residence time of the reactants in the reaction zone is in the range of a few seconds to hours, or about 0.5 min to about 60 min, or about 1 min to about 60 min, or about 3 min to about 60 min.

The acidity needs to be controlled to provide for suitable alkylation conditions. This can be done by adding a metal, an acid, or acid precursor, such as HCl, 2-chlorobutane, or tert-butyl chloride, for example. The metal, acid, or acid precursor can be added anywhere in the process prior to the addition of the olefin to the hydrocarbon (or hydrocarbon to the olefin). For example, it can be added to one of the feeds to the alkylation reaction zone, to the reaction zone, or to a recycle stream. Alternatively, the excess acid could be stripped from the fresh liquid Lewis acid with, for example, isobutane, nitrogen, or triethylsilane (TES), and the acid level could be controlled at the low level needed during the reaction. Another alternative is to reduce the pressure and add heat to remove the excess acid.

The paraffin or aromatic and olefin can be introduced separately or as a mixture. The molar ratio between the paraffin or aromatic and the olefin is in the range between 100:1 and 1:1, or 50:1 and 2:1, or 20:1 and 2:1.

In a semi-batch system, the paraffin or aromatic is introduced first, then the olefin is added, or a mixture of paraffin or aromatic and olefin can be introduced. The catalyst is measured in the reactor with respect to the amount of olefins, with a catalyst to olefin weight ratio between 0.1 and 10, or 0.2 and 5, or 0.5 and 2.

The heat generated by the reaction can be eliminated using any of the means known to the skilled person.

At the reactor outlet, the hydrocarbon phase is separated from the liquid Lewis acid phase by gravity settling based on density differences, or by other separation techniques known to those skilled in the art. The hydrocarbons are separated by distillation, and the starting hydrocarbon which has not been converted is recycled to the reaction zone.

The liquid Lewis acid can be present in the alkylation reaction zone in an amount of about 1 vol % to about 75 vol % of the total material in the reaction zone (i.e., the paraffin or aromatic, the olefin, and the liquid Lewis acid), or about 1 vol % to about 60 vol %, or about 1 vol % to about 50 vol %, or about 1 vol % to about 40 vol %, or about 1 vol % to about 30 vol %, or about 1 vol % to about 25 vol %, or about 1 vol % to about 20 vol %, or about 1 vol % to about 15 vol %, or about 1 vol % to about 10 vol %.

In some embodiments, the residence time needed for the process may affect the amount of liquid Lewis acid used. For example, a shorter residence time may require more liquid Lewis acid catalyst, while a longer residence time may require less liquid Lewis acid catalyst Typical alkylation conditions may include a catalyst volume in the reactor of from 1 vol % to 75 vol %, a temperature of from 0° C. to 100° C., a pressure of from 300 kPa to 2500 kPa, an isobutane to olefin molar ratio of from 2 to 20 and a residence time of 1 min to 1 hour.

The paraffin used in the alkylation process preferably comprises a paraffin having from 2 to 10 carbon atoms, or 4 to 8 carbon atoms, or 4 to 5 carbon atoms. The olefin used in the alkylation process preferably has from 2 to 10 carbon atoms, 3 to 8 carbon atoms, or 3 to 5 carbon atoms. One application of the process is to upgrade low value $C_4$ hydrocarbons to higher value alkylates.

To that extent, one specific embodiment is the alkylation of butanes with butylenes to generate $C_8$ compounds. Preferred products include trimethylpentane (TMP), and while other $C_8$ isomers are produced, one competing isomer is dimethylhexane (DMH). The quality of the product stream can be measured in the ratio of TMP to DMH, with a high ratio desired.

In another embodiment, the invention comprises passing an isoparaffin and an olefin to an alkylation reactor, where the alkylation reactor includes the liquid Lewis acid catalyst to react the olefin with the isoparaffin to generate an alkylate. The isoparaffin has from 4 to 10 carbon atoms, and the olefin has from 2 to 10 carbon atoms.

In another embodiment, an aromatic is used in the alkylation process. The aromatic typically comprises an aromatic have from 6 to 10 carbon atoms, or 6 to 8 carbon atoms. The olefin used in the alkylation process preferably has from 2 to 26 carbon atoms, or 4 to 26 carbon atoms, or 6 to 26 carbon atoms, or 8 to 26 carbon atoms, or 10 to 26 carbon atoms, or 2 to 20 carbon atoms, or 4 to 20 carbon atoms, or 6 to 20 carbon atoms, or 8 to 20 carbon atoms, or 10 to 20 carbon atoms, or 6 to 16 carbon atoms, or 8 to 16 carbon atoms, or 10 to 16 carbon atoms, or 10 to 14 carbon atoms.

The liquid Lewis acid can be regenerated using processes similar to those used for regenerating spent ionic liquid catalysts. Spent ionic liquid contains conjunct polymer which must be removed. A variety of methods for regenerating ionic liquids have been developed. For example, U.S. Pat. Nos. 7,651,970; 7,825,055; 7,956,002; 7,732,363, each of which is incorporated herein by reference, describe contacting ionic liquid containing the conjunct polymer with a reducing metal (e.g., Al), an inert hydrocarbon (e.g., hexane), and hydrogen and heating to about 100° C. to transfer the conjunct polymer to the hydrocarbon phase, allowing for the conjunct polymer to be removed from the ionic liquid phase. Another method involves contacting ionic liquid containing conjunct polymer with a reducing metal (e.g., Al) in the presence of an inert hydrocarbon (e.g. hexane) and heating to about 100° C. to transfer the conjunct polymer to the hydrocarbon phase, allowing for the conjunct polymer to be removed from the ionic liquid phase. See e.g., U.S. Pat. No. 7,674,739 B2; which is incorporated herein by reference. Still another method of regenerating the ionic liquid involves contacting the ionic liquid containing the conjunct polymer with a reducing metal (e.g., Al), HCl, and an inert hydrocarbon (e.g. hexane), and heating to about 100° C. to transfer the conjunct polymer to the hydrocarbon phase. See e.g., U.S. Pat. No. 7,727,925, which is incorporated herein by reference. The ionic liquid can be regenerated by adding a homogeneous metal hydrogenation catalyst (e.g., $(PPh_3)_3RhCl$) to ionic liquid containing conjunct polymer and an inert hydrocarbon (e.g. hexane), and introducing hydrogen. The conjunct polymer is reduced and transferred to the hydrocarbon layer. See e.g., U.S. Pat. No. 7,678,727, which is incorporated herein by reference. Another method for regenerating the ionic liquid involves adding HCl, isobutane, and an inert hydrocarbon to the ionic liquid containing the conjunct polymer and heating to about 100° C. The conjunct polymer reacts to form an uncharged complex, which transfers to the hydrocarbon phase. See e.g., U.S. Pat. No. 7,674,740, which is incorporated herein by reference. The ionic liquid could also be regenerated by adding a supported metal hydrogenation catalyst (e.g. Pd/C) to the ionic liquid containing the conjunct polymer and an inert hydrocarbon (e.g. hexane). Hydrogen is introduced and the conjunct polymer is reduced and transferred to the hydrocarbon layer. See e.g., U.S. Pat. No. 7,691,771, which is incorporated herein by reference. Still another method involves adding a suitable substrate (e.g. pyridine) to the ionic liquid containing the conjunct polymer. After a period of time, an inert hydrocarbon is added to wash away the liberated conjunct polymer. The ionic liquid precursor [butylpyridinium][Cl] is added to the ionic liquid (e.g. [butylpyridinium][$Al_2Cl_7$]) containing the conjunct polymer followed by an inert hydrocarbon. After mixing, the hydrocarbon layer is separated, resulting in a regenerated ionic liquid. See, e.g., U.S. Pat. No. 7,737,067, which is incorporated herein by reference. Another method involves adding ionic liquid containing conjunct polymer to a suitable substrate (e.g. pyridine) and an electrochemical cell containing two aluminum electrodes and an inert hydrocarbon. A voltage is applied, and the current measured to determine the extent of reduction. After a given time, the inert hydrocarbon is separated, resulting in a regenerated ionic liquid. See, e.g., U.S. Pat. No. 8,524,623, which is incorporated herein by reference. Ionic liquids can also be regenerated by contacting with silane compounds (U.S. application Ser. No. 14/269,943), borane compounds (U.S. application Ser. No. 14/269,978), Brønsted acids, (U.S. application Ser. No. 14/229,329), or $C_1$ to $C_{10}$ Paraffins (U.S. application Ser. No. 14/229,403), each of which is incorporated herein by reference.

EXAMPLES

Synthesis of LLA

In a nitrogen glovebox, aluminum trichloride (11.6 g, 87.1 mmol) was slowly added to dimethylacetamide while stirring (5.03 g, 57.7 mol). After stirring for 2.5 h, a homogeneous liquid resulted.

Alkylation Experiment with LLA

In a $N_2$ atmosphere, the LLA was loaded into a 300 ml autoclave containing a baffle. Prior to loading, the autoclave and baffle had been dried for several hours above 100° C. The number of acid sites in the LLA was adjusted to optimize the performance. (The number of acid sites can be adjusted by changing the catalyst loading or by changing the amount of acid or acid precursor added.) The autoclave was charged with 80 g isobutane and pressurized with 3.4 MPa(g) (500 psig) of nitrogen. The contents were stirred at 1500 rpm, and 8 g 2-butene was added over time (about 7.79 mL/h) at room temperature. After 8 min, the reaction mixture was allowed to settle, and the liquid product was sampled directly from the autoclave. The sample was passed through a silica column and then analyzed by gas chromatography. The results are shown in Table 1. (The groupings below include all isomers having the same carbon number.) The % butenes conversion was calculated using 100−(the weight of butenes in the product divided by the weight of butenes added). RONC is the Research Octane Number Calculated. TMP/DMH is the weight ratio of trimethylpentanes to dimethylhexanes in the product. The % Selectivity is (wt % of that paraffin)/(sum of wt % of the $C_5$ and larger products formed). The yield is (the mass of $C_5$ and larger products formed)/(the mass of the $C_4$ olefin added).

TABLE 1

| | 6.8 g LLA + 0.466 g 2-chlorobutane | 5.7 g LLA + 0.360 g 2-chlorobutane |
|---|---|---|
| Mol ratio Al:chlorobutane | 1:0.4 | 1:0.4 |
| Vol % IL | 3.5 | 2.7 |
| Reaction Time | 8 min | 8 min |
| i/o (mol ratio) | 8.0 | 8.6 |
| Butenes Conversion (%) | 99.9 | 99.9 |
| RONC | 94.0 | 94.6 |
| % Sel C8 | 74.8 | 76.2 |
| % Sel C9 | 7.9 | 8.13 |
| % Sel C5-7 | 17.31 | 15.66 |
| TMP/DMH | 9.5 | 10.4 |
| Yield (C5+/C4=) | 2.13 | 2.20 |

By the term "about," we mean within 10% of the value, or within 5%, or within 1%.

SPECIFIC EMBODIMENTS

While the following is described in conjunction with specific embodiments, it will be understood that this description is intended to illustrate and not limit the scope of the preceding description and the appended claims.

A first embodiment of the invention is a process comprising contacting a hydrocarbon feed comprising a paraffin or an aromatic with an olefin feed in the presence of a liquid Lewis acid catalyst in an alkylation reaction zone under alkylation conditions to form a reaction mixture comprising alkylation products and the liquid Lewis acid catalyst, wherein the liquid Lewis acid catalyst is a liquid reaction product of a donor molecule and a metal halide; separating the alkylation products from the liquid Lewis acid catalyst; and recovering the alkylation products. An embodiment of the invention is one, any or all of prior embodiments in this paragraph up through the first embodiment in this paragraph wherein the metal in the metal halide comprises Sn, Al, Zn, Mn, Fe, Ga, Cu, Ni, Co, In, or combinations thereof, and wherein the halide comprises Br, Cl, I, F, or combinations thereof. An embodiment of the invention is one, any or all of prior embodiments in this paragraph up through the first embodiment in this paragraph wherein the metal halide comprises $AlCl_3$, $AlCl_2Br$, $AlBr_3$, $GaCl_3$, $GaCl_2Br$, $FeCl_3$, $GaBr_3$, $InCl_3$, $InBr_3$, $InCl_2Br$, or combinations thereof. An embodiment of the invention is one, any or all of prior embodiments in this paragraph up through the first embodiment in this paragraph wherein the donor molecule comprises N,N-dimethylacetamide, N,N-dimethylformamide, N,N-dimethysulfoxide, caprolactam, N-methylcaprolactam, N-methylpyrrolidone, delta-valerolactone, tetrahydrofuran, diethyl ether, acetamide, caprolactone, delta-valerolactam, alpha-acetolactone, beta-propiolactone, gamma-butyrolactone, morpholine, beta-propiolactam, gamma-butyrolactam, delta-valerolactam, urea, trioctylphosphine oxide, thiourea, thioacetamide, N-methylthioacetamide, N,N-dimethylthioacetamide, trioctylphosphine, or combinations thereof. An embodiment of the invention is one, any or all of prior embodiments in this paragraph up through the first embodiment in this paragraph wherein a mole fraction of the metal halide in the liquid Lewis acid is greater than about 0.5 to less than about 1. An embodiment of the invention is one, any or all of prior embodiments in this paragraph up through the first embodiment in this paragraph further comprising adding a metal, an acid, or an acid precursor to the alkylation reaction zone. An embodiment of the invention is one, any or all of prior embodiments in this paragraph up through the first embodiment in this paragraph further comprising recovering the liquid Lewis acid catalyst to the alkylation reaction zone. An embodiment of the invention is one, any or all of prior embodiments in this paragraph up through the first embodiment in this paragraph further comprising recycling the liquid Lewis acid catalyst to the alkylation reaction zone. An embodiment of the invention is one, any or all of prior embodiments in this paragraph up through the first embodiment in this paragraph further comprising regenerating the liquid Lewis acid catalyst. An embodiment of the invention is one, any or all of prior embodiments in this paragraph up through the first embodiment in this paragraph wherein the alkylation conditions include a temperature of from about 0° C. to about 100° C., a pressure from about 0.3 MPa(g) to about 2.5 MPa(g), a hydrocarbon to olefin molar ratio from about 2:1 to about 20:1, and a residence time of about 1 min to about 1 hour. An embodiment of the invention is one, any or all of prior embodiments in this paragraph up through the first embodiment in this paragraph wherein when the hydrocarbon feed comprises the paraffin, the paraffin has 3 to 8 carbon atoms and the olefin feed comprises an olefin having 2 to 8 carbon atoms, and when the hydrocarbon feed comprises the aromatic, the aromatic has 6 to 10 carbon atoms and the olefin feed has 8 to 26 carbon atoms. An embodiment of the invention is one, any or all of prior embodiments in this paragraph up through the first embodiment in this paragraph wherein the liquid Lewis acid catalyst is present in an amount between about 1 vol % and about 75 vol % of a total volume of material in the alkylation reaction zone.

A second embodiment of the invention is a process comprising contacting a hydrocarbon feed with an olefin feed in the presence of a liquid Lewis acid catalyst in an alkylation reaction zone under alkylation conditions to form a reaction mixture comprising alkylation products and the liquid Lewis acid catalyst, wherein the liquid Lewis acid catalyst is a liquid reaction product of a donor molecule and a metal halide, and wherein the hydrocarbon feed comprises a paraffin having 3 to 8 carbon atoms and wherein the olefin feed has 2 to 8 carbon atoms, or wherein the hydrocarbon feed comprises a aromatic having 6 to 10 carbon atoms and wherein the olefin feed has 8 to 26 carbon atoms; separating the alkylation products from the liquid Lewis acid catalyst; recovering the alkylation products; and recovering the liquid Lewis acid catalyst. An embodiment of the invention is one, any or all of prior embodiments in this paragraph up through the second embodiment in this paragraph wherein the metal in the metal halide comprises Sn, Al, Zn, Mn, Fe, Ga, Cu, Ni, Co, In, or combinations thereof, and wherein the halide comprises Br, Cl, I, F, or combinations thereof. An embodiment of the invention is one, any or all of prior embodiments in this paragraph up through the second embodiment in this paragraph wherein the metal halide comprises $AlCl_3$, $AlCl_2Br$, $AlBr_3$, $GaCl_3$, $GaCl_2Br$, $FeCl_3$, $GaBr_3$, $InCl_3$, $InBr_3$, $InCl_2Br$, or combinations thereof. An embodiment of the invention is one, any or all of prior embodiments in this paragraph up through the second embodiment in this paragraph wherein the donor molecule comprises N,N-dimethylacetamide, N,N-dimethylformamide, N,N-dimethysulfoxide, caprolactam, N-methylcaprolactam, N-methylpyrrolidone, delta-valerolactone, tetrahydrofuran, diethyl ether, acetamide, caprolactone, delta-valerolactam, alpha-acetolactone, beta-propiolactone, gamma-butyrolactone, morpholine, beta-propiolactam, gamma-butyrolactam, delta-valerolactam, urea, trioctylphosphine oxide, thiourea, thioacetamide, N-methylthioacetamide, N,N-dimethylthioacetamide, trioctylphosphine, or combinations thereof. An embodiment of the invention is one, any or all of prior embodiments in this paragraph up through the second embodiment in this paragraph wherein a mole fraction of metal halide in the liquid Lewis acid is greater than about 0.5 to less than about 1. An embodiment of the invention is one, any or all of prior embodiments in this paragraph up through the second embodiment in this paragraph further comprising adding a metal, an acid, or an acid precursor to the alkylation reaction zone. An embodiment of the invention is one, any or all of prior embodiments in this paragraph up through the second embodiment in this paragraph further comprising at least one of recycling the liquid Lewis acid catalyst to the alkylation reaction zone. An embodiment of the invention is one, any or all of prior embodiments in this paragraph up through the second embodiment in this paragraph further comprising regenerating the liquid Lewis acid catalyst. An embodiment of the invention is one, any or all of prior embodiments in this paragraph up through the second embodiment in this paragraph wherein the alkylation conditions include a temperature of from about 0° C. to about 100° C., a pressure from about 0.3 MPa(g) to about 2.5 MPa(g), an isobutane to olefin molar ratio from about 2:1 to about 20:1, and a residence time of about 1 min to about 1 hour; and wherein liquid Lewis acid catalyst is present in an amount between about 1 vol % and about 75 vol % of the total volume of material in the alkylation reaction zone.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. An alkylation process comprising:
    contacting a hydrocarbon feed comprising a butane with an olefin feed comprising a butene in the presence of a liquid Lewis acid catalyst and in the absence of hydrofluoric acid in an alkylation reaction zone under alkylation conditions to form a biphasic reaction mixture comprising alkylation products comprising trimethylpentanes and the liquid Lewis acid catalyst, wherein the liquid Lewis acid catalyst is a liquid reaction product of a donor molecule and a metal halide, wherein the metal in the metal halide is Al, wherein the donor molecule comprises caprolactam, N-methylcaprolactam, delta-valerolactone, tetrahydrofuran, caprolactone, alpha-acetolactone, beta-propiolactone, gamma-butyrolactone, morpholine, beta-propiolactam, gamma-butyrolactam, delta-valerolactam, or combinations thereof, wherein a mole fraction of the metal halide in the liquid Lewis acid is greater than about 0.5 to less than about 1;
    separating the biphasic reaction mixture into the alkylation products and the liquid Lewis acid catalyst; and
    recovering the alkylation products.

2. The process of claim 1 wherein the halide in the metal halide comprises Br, Cl, I, F, or combinations thereof.

3. The process of claim 1 wherein the metal halide comprises AlCl$_3$, AlCl$_2$Br, AlBr$_3$, or combinations thereof.

4. The process of claim 1 wherein the donor molecule comprises caprolactam, N-methylcaprolactam, delta-valerolactone, tetrahydrofuran, caprolactone, alpha-acetolactone, beta-propiolactone, gamma-butyrolactone, morpholine, beta-propiolactam, gamma-butyrolactam, delta-valerolactam, or combinations thereof.

5. The process of claim 1 further comprising adding a metal, an acid, or an acid precursor to the alkylation reaction zone.

6. The process of claim 1 further comprising recovering the liquid Lewis acid catalyst.

7. The process of claim 1 further comprising recycling the liquid Lewis acid catalyst to the alkylation reaction zone.

8. The process of claim 1 further comprising regenerating the liquid Lewis acid catalyst.

9. The process of claim 1 wherein the alkylation conditions include a temperature of from about 0° C. to about 100° C., a pressure from about 0.3 MPa(g) to about 2.5 MPa(g), a hydrocarbon to olefin molar ratio from about 2:1 to about 20:1, and a residence time of about 1 min to about 1 hour.

10. The process of claim 1 wherein the liquid Lewis acid catalyst is present in an amount between about 1 vol % and about 75 vol % of a total volume of material in the alkylation reaction zone.

11. An alkylation process comprising:
    contacting a hydrocarbon feed with an olefin feed in the presence of a liquid Lewis acid catalyst and in the absence of hydrofluoric acid in an alkylation reaction zone under alkylation conditions to form a biphasic reaction mixture comprising alkylation products and the liquid Lewis acid catalyst, wherein the liquid Lewis acid catalyst is a liquid reaction product of a donor molecule and a metal halide, wherein the donor molecule comprises caprolactam, N-methylcaprolactam, delta-valerolactone, tetrahydrofuran, caprolactone, alpha-acetolactone, beta-propiolactone, gamma-butyrolactone, morpholine, beta-propiolactam, gamma-butyrolactam, delta-valerolactam, or combinations thereof, and wherein the hydrocarbon feed comprises a paraffin having 3 to 8 carbon atoms and wherein the olefin feed has 2 to 8 carbon atoms;
    separating the biphasic reaction mixture into the alkylation products and the liquid Lewis acid catalyst;
    recovering the alkylation products; and
    recovering the liquid Lewis acid catalyst.

12. The process of claim 11 wherein the metal in the metal halide comprises Sn, Al, Zn, Mn, Fe, Ga, Cu, Ni, Co, In, or combinations thereof, and wherein the halide comprises Br, Cl, I, F, or combinations thereof.

13. The process of claim 11 wherein the metal halide comprises AlCl$_3$, AlCl$_2$Br, AlBr$_3$, GaCl$_3$, GaCl$_2$Br, FeCl$_3$, GaBr$_3$, InCl$_3$, InBr$_3$, InCl$_2$Br, or combinations thereof.

14. The process of claim 11 wherein a mole fraction of metal halide in the liquid Lewis acid is greater than about 0.5 to less than about 1.

15. The process of claim 11 further comprising adding a metal, an acid, or an acid precursor to the alkylation reaction zone.

16. The process of claim 11 further comprising at least one of:
    recycling the liquid Lewis acid catalyst to the alkylation reaction zone; and
    regenerating the liquid Lewis acid catalyst.

17. The process of claim 11 wherein the alkylation conditions include a temperature of from about 0° C. to about 100° C., a pressure from about 0.3 MPa(g) to about 2.5 MPa(g), an isobutane to olefin molar ratio from about 2:1 to about 20:1, and a residence time of about 1 min to about 1 hour; and wherein liquid Lewis acid catalyst is present in an amount between about 1 vol % and about 75 vol % of the total volume of material in the alkylation reaction zone.

18. An alkylation process comprising:
contacting a hydrocarbon feed comprising a paraffin or an aromatic with an olefin feed in the presence of a liquid Lewis acid catalyst in an alkylation reaction zone under alkylation conditions to form a biphasic reaction mixture comprising alkylation products and the liquid Lewis acid catalyst, wherein the liquid Lewis acid catalyst is a liquid reaction product of a donor molecule and a metal halide, wherein the metal in the metal halide is Al, wherein the donor molecule is a Lewis base capable of donating electrons to the metal, wherein the donor molecule comprises caprolactam, N-methylcaprolactam, delta-valerolactone, tetrahydrofuran, caprolactone, alpha-acetolactone, beta-propiolactone, gamma-butyrolactone, morpholine, beta-propiolactam, gamma-butyrolactam, delta-valerolactam, or combinations thereof, wherein a mole fraction of the metal halide in the liquid Lewis acid is greater than about 0.5 to less than about 1;
separating the biphasic reaction mixture into the alkylation products and the liquid Lewis acid catalyst; and
recovering the alkylation products.

19. The process of claim 18 wherein the donor molecule comprises caprolactam, N-methylcaprolactam, delta-valerolactone, tetrahydrofuran, caprolactone, alpha-acetolactone, beta-propiolactone, gamma-butyrolactone, morpholine, beta-propiolactam, gamma-butyrolactam, delta-valerolactam, or combinations thereof.

* * * * *